United States Patent [19]

Chadwick et al.

[11] Patent Number: 5,326,896
[45] Date of Patent: Jul. 5, 1994

[54] CONVERSION OF DIRECT PROCESS HIGH-BOILING COMPONENT TO SILANE MONOMERS IN THE PRESENCE OF HYDROGEN GAS

[75] Inventors: Kirk M. Chadwick, S. Glamorgan, United Kingdom; Ajay K. Dhaul, Carrollton, Ky.; Roland L. Halm, Madison; Richard G. Johnson, Hanover, both of Ind.

[73] Assignee: Dow Corning Corporation, Midland, Mich.

[21] Appl. No.: 91,933

[22] Filed: Jul. 14, 1993

[51] Int. Cl.$^5$ .............................. C07F 7/08
[52] U.S. Cl. .................... 556/466; 556/468
[58] Field of Search ............... 556/468, 466

[56] References Cited

U.S. PATENT DOCUMENTS

| | | |
|---|---|---|
| 2,380,995 | 8/1945 | Rochow . |
| 2,488,487 | 11/1949 | Barry et al. . |
| 2,598,435 | 5/1952 | Mohler et al. . |
| 2,681,355 | 6/1954 | Barry et al. . |
| 2,709,176 | 5/1955 | Bluestein . |
| 2,842,580 | 7/1958 | Gilbert . |
| 3,006,943 | 10/1961 | Nitzsche et al. ............ 556/468 |
| 3,432,537 | 3/1969 | Guinet et al. ............... 556/468 |
| 3,639,105 | 2/1972 | Atwell . |
| 4,059,608 | 11/1977 | Calas et al. . |
| 4,079,071 | 3/1978 | Neale . |
| 4,461,908 | 7/1984 | Takamizawa et al. ......... 556/468 X |
| 4,578,495 | 3/1986 | Soula et al. .................. 556/468 |
| 4,958,040 | 9/1990 | Yoshioka et al. ............ 556/468 X |
| 5,210,255 | 5/1993 | Kalchauer et al. ........... 556/468 |

OTHER PUBLICATIONS

Takeda et al., Kogyo Kagaku Zasshi (Journal of Industrial Chemistry) vol. 60, No. 11, pp. 1392–1395 (1957).

*Primary Examiner*—Paul F. Shaver
*Attorney, Agent, or Firm*—William F. Boley

[57] ABSTRACT

The present invention is a process for converting a high-boiling component resulting from the reaction of an organochloride with silicon into commercially more desirable monosilanes. The process comprises contacting the high-boiling component with hydrogen gas at a temperature within a range having a lower limit greater than 250° C. and an upper limit of 1000° C. Yield of the present process may be improved by use of a catalyst selected from a group consisting of activated carbon, platinum metal, platinum supported on alumina, palladium supported on carbon, $SbCl_5$, $H_2PtCl_6$, $BCl_3$, $AlCl_3$, and $AlCl_3$ supported on a support material selected from a group consisting of carbon, alumina, and silica. In a preferred embodiment of the present process the process is run at a pressure within a range of about 250–1000 psig. The present process is preferential for the production of diorganodichlorosilane in relation to organotrichlorosilane in the monosilane product.

31 Claims, No Drawings

CONVERSION OF DIRECT PROCESS HIGH-BOILING COMPONENT TO SILANE MONOMERS IN THE PRESENCE OF HYDROGEN GAS

BACKGROUND OF INVENTION

The present invention is a process for converting a high-boiling component resulting from the reaction of an organochloride with silicon into commercially more desirable monosilanes. The process comprises contacting the high-boiling component with hydrogen gas at a temperature within a range having a lower limit greater than 250° C. and an upper limit of 1000° C. Yield of the present process may be improved by use of a catalyst selected from a group consisting of activated carbon, platinum metal, platinum supported on alumina, palladium supported on carbon, $SbCl_5$, $H_2PtCl_6$, $BCl_3$, $AlCl_3$, and $AlCl_3$ supported on a support material selected from a group consisting of carbon, alumina, and silica. In a preferred embodiment of the present process the process is run at a pressure within a range of about 250-1000 psig. A significant advantage of the present process is that it is preferential for the production of diorganodichlorosilane in relation to organotrichlorosilane in the monosilane product.

The high-boiling component useful in the present process results from a process typically referred to as the "Direct Process", where an organohalide is reacted with silicon metalloid in the presence of a suitable catalyst to form monosilanes. The Direct Process as described by, for example, Rochow, U.S. Pat. No. 2,380,995, issued Aug. 7, 1945, and Barry et al., U.S. Pat. No. 2,488,487, issued Nov. 15, 1949, is the main commercial process by which organohalosilanes (i.e. monosilanes), for example, dimethyldichlorosilane and trimethylchlorosilane are formed. These organohalosilanes are reactive compounds which can undergo numerous reactions to form a variety of useful silicon containing compounds and polymers. In typical commercial direct processes the process is optimized to produce the diorganodihalosilane, since this monosilane can be hydrolyzed to form polysiloxane polymers having a broad range of commercial applications. Polysiloxane polymers are useful, for example, as heat transfer fluids, lubricants, and the like and can be further processed, for example, to form silicone elastomers, resins, sealants, and adhesives.

Operation of the Direct Process results not only in the production of the desirable monosilanes, but also in a high boiling component typically considered to be all materials with a boiling point higher than the particular diorganodihalosilane produced in the process. The high-boiling component is a complex mixture that includes compounds containing SiSi, SiOSi, SiCSi, SiCCSi, and SiCCCSi linkages in the molecules. Some typical compounds found in a high-boiling component are described, for example, in Mohler et al., U.S. Pat. No. 2,598,435, issued May 27, 1952, and Barry et al., U.S. Pat. No. 2,681,355, issued Jun. 15, 1954. The high-boiling component may also comprise silicon containing solids and soluble and insoluble compounds of copper, aluminum, and zinc.

In current commercial operations for performing the Direct Process, the high-boiling component can constitute as much as ten percent of the resultant product. Therefore, it is desirable to convert the high-boiling component into commercially desirable products to both reduce low value by-products and to improve raw material utilization.

Mohler, U.S. Pat. No. 2,598,435, issued May 27, 1952, describes a process for converting methylpolysilanes present in a Direct Process residue to monosilanes, the process comprises heating the residue at a temperature above 250° C. and below the decomposition point of the formed monosilanes.

Barry. U.S. Pat. No. 2,681,355, issued Jun. 15, 1954, observed that the process taught in Mohler, U.S. Pat. No. 2,598,435, can result in significant coking of the reactor making the process unsuitable for commercial cracking processes. Barry, supra, teaches that this coking can be reduced if the Direct Process residue is contacted with at least four percent by weight hydrogen chloride at a temperature from 200° C. to 900° C. Barry also suggests that the process can be run in a reactor packed with either an inert material such as quartz or a catalytic material such as activated alumina or silica alumina.

Bluestein, U.S. Pat. No. 2,709,176, issued May 25, 1955, reports a process for converting the polysilanes present in a Direct Process residue into monosilanes by the use of a tertiary organic amine catalyst. Bluestein reports that when the Direct Process residue is contacted with a hydrogen halide and a tertiary organic amine catalyst, the process can be conducted at temperatures of about 75° C. to 150° C. with acceptable yields of monosilanes being obtained.

Gilbert. U.S. Pat. No. 2,842,580, issued Jul. 8, 1958, reports a process for converting the polysilanes present in a Direct Process residue into monosilanes by the use of quaternary ammonium halide and quaternary phosphonium halide compounds as catalysts. The process of Gilbert is run in the absence of hydrogen chloride, as described by Bluestein supra, and is reported to provide monosilanes with reduced levels of hydrogen bonded to the silicon atoms.

Atwell et al., U.S. Pat. No. 3,639,105, issued Feb. 1, 1972, describe a process where hydrosilanes are produced by contacting disilane with hydrogen gas under pressure. The resulting mixture is heated in the presence of a transition metal catalyst at temperatures within a range of 25° C. to 250° C. Atwell et al. teach that at temperatures in excess of 250° C. catalyst and/or disilane decomposition tends to occur which deleteriously affects the reaction.

Calas et al., U.S. Pat. No. 4,059,608, teach a process for hydrogenating disilanes, where a catalyst system containing an aprotic compound and a nickel catalyst is used. Calas et al. teach the process can be conducted at a temperature within a range of 50 to 200° C. In the provided examples the ratio of dimethyldichlorosilane to methytrichlorosilane varies between 0.7 to 1.0.

Neale, U.S. Pat. No. 4,079,071, issued Mar. 14, 1978, teaches a process for preparing high yields of hydrosilanes by reacting methylchloropolysilanes with hydrogen gas under pressure at a temperature of from about 25° C. to about 350° C. in the presence of a copper catalyst.

Takeda et al.. Kogyo Kagaku zasshi (Journal of Industrial Chemistry), Vol. 60, No. 11, p. 1392-1395 (1957), described the use of alumina, carbon, and pumice as catalyst for the catalytic cracking of disilane in a hydrogen stream.

An objective of the present process is to provide a process for the conversion of a high-boiling component from the direct process to monosilanes. A second objective is to provide a process preferential for the production of diorganodichlorosilane in relation to organotrichlorosilane in the monosilane product.

SUMMARY OF INVENTION

The present invention is a process for converting a high-boiling component resulting from the reaction of organochlorides with silicon into commercially more desirable monosilanes. The process comprises contacting the high-boiling component with hydrogen gas at a temperature within a range having a lower limit greater than 250° C. and an upper limit of 1000° C. Yield of the present process may be improved by use of a catalyst selected from a group consisting of activated carbon, platinum metal, platinum supported on alumina, palladium supported on carbon. $SbCl_5$, $H_2PtCl_6$, $BCl_3$, $AlCl_3$, and $AlCl_3$ supported on a support material selected from a group consisting of carbon, alumina, and silica. In a preferred embodiment of the present process the process is run at a pressure within a range of about 250–1000 psig. The present process is preferential for the production of diorganodichlorosilane in relation to organotrichlorosilane in the monosilane product.

DESCRIPTION OF INVENTION

The present invention is a process for converting a high-boiling component resulting from the reaction of an organochloride with silicon metalloid (hereafter referred to as silicon) to monosilanes. The process comprises contacting a high-boiling component, resulting from the reaction of an organochloride with silicon, and hydrogen gas at a temperature within a range having a lower limit greater than 250° C. and an upper limit of 1000° C. Yield of the present process may be improved by use of a catalyst selected from a group consisting of activated carbon, platinum metal, platinum supported on alumina, palladium supported on carbon, $SbCl_5$, $H_2PtCl_6$, $BCl_3$, $AlCl_3$, and $AlCl_3$ supported on a support material selected from a group consisting of carbon, alumina, and silica. In a preferred embodiment of the present process the process is run at a pressure within a range of about 250 psig to 1000 psig.

The present process may be run in any standard type reactor for contacting chlorosilanes with a gas such as hydrogen. The process may be run as a batch process, semi-continuous, or continuous process. The process can be run, for example, in a fixed-bed reactor, a stirred-bed reactor, or a fluidized-bed reactor.

The present process is useful for converting a high-boiling component resulting from the reaction of an organochloride with silicon to monosilanes. The term "high-boiling component" refers to those materials with a boiling point above that of the diorganodichlorosilane formed by the reaction of the organochloride with silicon. For example when methyl chloride is reacted with silicon, the diorganodichlorosilane will be dimethyldichlorosilane and the high-boiling component will comprise those materials having a boiling point greater than that of dimethyldichlorosilane, i.e. greater than about 70° C.

In a typical process for reacting an organochloride with silicon, the process is conducted at a temperature of about 270° C. to 350° C., in the presence of a suitable catalyst, and gaseous products and unreacted feed are continuously removed from the process. The removed gaseous products and unreacted feed are subsequently distilled to remove monosilanes leaving a high-boiling component.

The high-boiling component is a complex mixture that can include compounds containing SiSi. SiOSi. SiCSi, SiCCSi. and SiCCCSi linkages alone or in combination in each molecule. The high-boiling component can include silicon containing solids and soluble and insoluble compounds of copper, aluminum, and zinc. The high-boiling component may contain, for example, organic substituted and non-organic substituted silanes, disilanes, trisilanes, disiloxanes, silane oligomers, siloxane oligomers, silalkylenes, and silicon containing solids, all of which may be converted to monosilanes by the present process.

The present process is useful for converting polysilanes in the high-boiling component to monosilanes, where the polysilanes are described by formula $R_aH_bSi_nCl_{2n+2-a-b}$ and where each R is a radical independently selected from a group consisting of alkyls comprising one to six carbon atoms, $n=2$ to 20, $a=0$ to $2n+2$, $b=0$ to $2n+2$, and $a+b=0$ to $2n+2$.

The polysilanes useful in the present process can consist of n number of silicon atoms where n is an integer from two to 20. Preferred is when n equals two. The polysilanes can be substituted with $a=0$ to $2n+2$ number of R radicals, where each R is independently selected from a group consisting of alkyls of one to six carbon atoms. The radical R can be, for example, methyl, ethyl, propyl, and t-butyl. Preferred is when R is methyl.

The polysilanes in the high-boiling component can contain b number of hydrogen atoms substituted on the silicon atoms, where $b=0$ to $2n+2$.

The polysilanes in the high-boiling component can contain from zero to $2n+2$ chlorine atoms.

The high-boiling component can contain silalkylenes, where each silalkylene can comprise one or more silakylene bonds described by formula $Si(C)_zSi$ and z is an integer from one to about six. Preferred is when z is an integer from one to three. The silicon atoms of the silalkylene molecules can be further substituted with the radical R, where R is as previously described, with chloride, and with hydrogen. Preferred is when the silicon atoms of the silalkylenes are substituted with methyl.

The preferred high-boiling component is one resulting from the reaction of methyl chloride with silicon, the high-boiling component having a boiling point greater than about 70° C. This high-boiling component can contain, for example, $Me_2ClSiSiMe_2Cl$, $Me_2ClSiSiMeCl_2$, $MeCl_2SiSiMeCl_2$, $Me_2ClSiSi(Me)(Cl)SiMeCl_2$, $Me_2ClSiCH_2SiMe_2Cl$, $Me_2ClSiCH_2SiMeCl_2$, $MeCl_2SiCH_2SiMeCl_2$, $Me_2ClSi(CH_2)_2SiMeCl_2$, $Me_2ClSi(CH_2)_3SiMeCl_2$, $Me_2ClSiCH_2Si(Me)(Cl)SiMeCl_2$, $Me_2ClSiCH_2Si(Me)(Cl)CH_2SiMeCl_2$, and $Me_2ClSiOSiMeCl_2$, where Me is methyl, all of which may be converted to monosilanes by the present process.

The high-boiling component is contacted with hydrogen gas, where the ratio of the weight of high-boiling component added to the reactor to the weight of hydrogen gas added to the reactor is within a range of about 0.1:1 to 1000:1. Preferred is where the ratio of the weight of high-boiling component to the weight of hydrogen gas is within a range of about 1:1 to 500:1.

The present process can be run at a pressure within a range of about zero psig to 3,000 psig. A preferred pressure is within a range of about 250 psig to 1000 psig.

Generally, pressures within the preferred range favor the production of the diorganodichlorosilane over the organotrichlorosilane.

The process is conducted at a temperature within a range having a lower limit greater than 250° C. and an upper limit of 1000° C. A preferred temperature is within a range of about 270° C. to 650° C.

The process may be conducted in the presence of a catalyst selected from a group consisting of activated carbon, platinum metal, platinum supported on alumina, palladium supported on carbon, $SbCl_5$, $H_2PtCl_6$, $BCl_3$, $AlCl_3$, and $AlCl_3$ supported on a support material selected from a group consisting of carbon, alumina, and silica.

The weight of catalyst in relation to the weight of high-boiling component and hydrogen gas added to the process will depend upon such factors as the type of catalyst, the chemical composition of the high-boiling component, the process temperature, and the type of reactor employed.

The optimum contact time for the high-boiling component and hydrogen gas with the catalyst will depend, for example, on factors such as the type of catalyst, chemical composition of the high-boiling component, and the degree of conversion and product selectivity desired. In general contact times within a range of about one second to five hours are considered useful. Longer contact times may be employed, but appear to offer no advantage and may result in excessive scission of silicon-carbon bonds and silicon-hydrogen bonds present in the monosilanes. A preferred contact time in a continuous-reactor system is within a range of about one second to two hours.

If desired, the monosilane containing product of the present process can be further separated by standard means, for example, distillation to separate the monosilanes from a high-boiling component and the high-boiling component recycled to the process.

Monosilanes which can be produced by the present process are described by the formula $R_xH_ySiCl_{4-x-y}$, where R is as previously described (i.e. each R is independently selected from a group consisting of alkyls comprising one to six carbon atoms); x=0, 1, 2, or 3; y=0, 1, or 2 and x+y=0, 1, 2, 3, or 4. The preferred monosilanes produced in the process are triorganochlorosilanes, diorganodichlorosilanes and organodichlorosilanes. Even more preferred is when the ratio of diorganodichlorosilane to organotrichlorosilane is greater than about 1.0 in the monosilane product.

The following examples are provided to facilitate understanding and to demonstrate the effectiveness of the present invention. These examples are not intended to limit the scope of the claims provided herein.

Example 1

Not within the scope of the present invention. A high-boiling component resulting from the reaction of methyl chloride with silicon was contacted with hydrogen chloride. The reactor consisted of a 2.5 cm diameter by 50 cm length quartz tube maintained at about 500° C. The high-boiling component comprised by weight, 55% methychlorodisilane, 5% disilmethylenes, 35% other polysilanes and silalkylenes, and 5% silicon containing solids. The high-boiling component was fed at a rate of 117 g/h to the reactor and hydrogen chloride was fed to the reactor at 50 g/h. The process was conducted for one hour with gaseous product exiting the reactor being collected in a cold condenser. The condensed product was analyzed by gas chromatography using a thermal conductivity detector (GC-TC) and found to consist of 59 weight percent chlorosilane monomers. Chlorosilane monomers detected included $HSiCl_3$, $SiCl_4$, $MeHSiCl_2$, $Me_3SiCl$, $MeSiCl_3$, and $Me_2SiCl_2$. The $Me_2SiCl_2$ and $MeSiCl_3$ comprised 43 weight percent of the monosilane product. The ratio of $Me_2SiCl_2$ to $MeSiCl_3$ was about 0.6. Other species detected in the condensed product included methylchlorodisilanes, disilmethylenes, polysilanes, and silalkylenes.

Example 2

A high-boiling component resulting from the reaction of methyl chloride with silicon was contacted with hydrogen gas. The process was conducted similar to that described in Example 1, with the high-boiling component composition and reactor design being the same. The process was conducted at a temperature of 750° C. The high-boiling component was fed to the reactor at a rate of 91 g/h and hydrogen gas was fed to the reactor at a rate of 3 g/h. The process was conducted for one hour with gaseous product exiting the reactor being collected and analyzed as described in Example 1. The collected product was found to comprise 50 weight percent chlorosilane monomers and included $MeSiCl_3$, $Me_2SiCl_2$, $Me_2HSiCl$, $HSiCl_3$, $SiCl_4$, $MeHSiCl_2$, and $Me_2SiCl_3$. The $Me_2SiCl_2$ and $MeSiCl_3$ comprised 78 weight percent of the monosilane product. The ratio of $Me_2SiCl_2$ to $MeSiCl_3$ was 1.3. Other species detected in the monosilane product included methylchlorodisilanes, disilmethylenes, and other high-boiling silicon containing polymer species.

Example 3

A high-boiling component resulting from the reaction of methyl chloride with silicon was contacted with hydrogen gas in the presence of a platinum supported on alumina catalyst. The process was conducted similar to that described in Example 1, with the high-boiling component composition and reactor design being the same. The reactor temperature was 500° C. The reactor was packed with 17 g of 1% platinum by weight) supported on 1.6 mm alumina spheres (UOP Inc., Tarrytown. N.Y.). The high-boiling component was fed to the reactor at a rate of 85 g/h and hydrogen was fed to the reactor at a rate of 3 g/h. The process was conducted for one hour with gaseous products exiting the reactor being collected and analyzed as described in Example 1.

The collected product was determined to consist of similar species as those described in Example 2. Of the product collected, 50 weight percent was chlorosilane monomers. The $Me_2SiCl_2$ and $MeSiCl_3$ comprised 75 weight percent of the monosilane product. The ratio of $Me_2SiCl_2$ to $MeSiCl_3$ was 1.6.

Example 4

A high-boiling component resulting from the reaction of methyl chloride with silicon was contacted with hydrogen gas at a reactor pressure of 1,000 psig for 37 minutes.

The reactor consisted of a 450 mL Hastaloy C pressure reactor. About 230 g of a high-boiling component, as described in Example 1, was added to the reactor along with 0.8 g of hydrogen gas. The reactor was maintained at 300° C. and approximately 1,000 psig for 37 minutes. After the reaction period the reactor was vented to a condenser and the collected product analyzed as described in Example 1.

The collected product was determined to consist of similar species as those described in Example 2. Of the product collected, 66 weight percent was chlorosilane monomers. The $Me_2SiCl_2$ and $MeSiCl_3$ comprised 82 weight percent of the monosilane product. The ratio of $Me_2SiCl_2$ to $MeSiCl_3$ was 2.7.

Example 5

A high-boiling component resulting from the reaction of methyl chloride with silicon was contacted with hydrogen gas at a reactor pressure of 1,000 psig for two minutes.

The reactor consisted of a 450 mL Hastaloy C pressure reactor. About 260 g of a high-boiling component, as described in Example 1, was added to the reactor along with 0.7 g of hydrogen gas. The reactor was maintained at 325° C. and approximately 1,000 psig for two minutes. After the reaction period the reactor was vented to a condenser and the collected product analyzed as described in Example 1.

The collected product was determined to consist of similar species as those described in Example 2. Of the product collected, 50 weight percent was chlorosilane monomers. The $Me_2SiCl_2$ and $MeSiCl_3$ comprised 85 weight percent of the monosilane product. The ratio of $Me_2SiCl_2$ to $MeSiCl_3$ was 4.1.

Example 6

A high-boiling component resulting from the reaction of methyl chloride with silicon was contacted with hydrogen gas in the presence of activated carbon catalyst. The process was conducted similar to that described in Example 1, with the high-boiling component composition and reactor design being the same. The reactor temperature was 500° C. The reactor was packed with 17 g of Calgon BPL 1 mm by 3.3 mm activated carbon pellets (Calgon, Pittsburgh. Pa.). The high-boiling component was fed to the reactor at a rate of 101 g/h and hydrogen was fed to the reactor at a rate of 3 g/h. The process was conducted for one hour with gaseous products exiting the reactor being collected and analyzed as described in Example 1.

The collected product was determined to consist of similar species as those described in Example 2. Of the product collected, 36 weight percent was chlorosilane monomers. The $Me_2SiCl_2$ and $MeSiC_3$ comprised 91 weight percent of the monosilane product. The ratio of $Me_2SiCl_2$ to $MeSiCl_3$ was 1.5.

We claim:

1. A process for converting a high-boiling component resulting from the reaction of an organochloride with silicon, to monosilanes, the process comprising: contacting a high-boiling component, resulting from the reaction of an organochloride with silicon, and hydrogen gas at a temperature within a range having a lower limit greater than 250° C. and an upper limit of 1000° C.

2. A process according to claim 1, where the temperature is within a range of about 270° C. to 650° C.

3. A process according to claim 1, where the high-boiling component and hydrogen are contacted at a pressure within a range of about zero psig to 3,000 psig.

4. A process according to claim 1, where the high-boiling component and hydrogen are contacted at a pressure within a range of about 250 psig to 1,000 psig.

5. A process according to claim 1, where the ratio of the weight of the high-boiling component to the weight of the hydrogen gas is within a range of about 0.1:1 to 1000:1.

6. A process according to claim 1, where the ratio of the weight of the high-boiling component to the weight of the hydrogen gas is within a range of about 1:1 to 500:1.

7. A process according to claim 1, where the high-boiling component results from the reaction of methyl chloride with silicon.

8. A process according to claim 1, where the high-boiling component comprises polysilanes and silalkylenes.

9. A process according to claim 1, where the high-boiling component comprises polysilanes described by formula $R_aH_bSi_nCl_{2n+2-a-b}$, where each R is a radical independently selected from a group consisting of alkyls comprising one to six carbon atoms, n=2 to 20, a=0 to 2n+2, b=0 to 2n+2, and a+b=0 to 2n+2.

10. A process according to claim 1, where the high-boiling component comprises silalkylenes comprising one or more silalkylene bonds described by formula $Si(C)_zSi$ and z=1, 2, or 3.

11. A process according to claim 1, where the high-boiling component comprises soluble and insoluble compounds of copper, aluminum, and zinc.

12. A process according to claim 1, where the monosilanes comprise diorganodichlorosilane and organotrichlorosilane and the ratio of the diorganodichlorosilane to the organotrichlorosilane is greater than about 1.0.

13. A process for converting a high-boiling component resulting from the reaction of an organochloride with silicon, to monosilanes, the process comprising: contacting a high-boiling component, resulting from the reaction of an organochloride with silicon, and hydrogen gas at a temperature within a range having a lower limit greater than 250° C. and an upper limit of 1000° C., in the presence of a catalyst selected from a group consisting of activated carbon, platinum metal, platinum support on alumina, palladium supported on carbon, $AlCl_3$, $SbCl_5$, $H_2PtCl_6$, $BCl_3$, $AlCl_3$, and $AlCl_3$ supported on a support material selected from a group consisting of carbon, alumina, and silica.

14. A process according to claim 13, where the catalyst is selected from a group consisting of platinum metal, platinum supported on alumina, palladium supported on carbon, $AlCl_3$, $SbCl_5$, $H_2PtCl_6$, $BCl_3$, $AlCl_3$, and $AlCl_3$ supported on a support material selected from a group consisting of carbon, alumina, and silica.

15. A process according to claim 13, where the catalyst is selected from a group consisting of activated carbon and platinum metal supported on alumina.

16. A process according to claim 13, where the catalyst is activated carbon.

17. A process according to claim 13, where the temperature is within a range of about 270° C. to 650° C.

18. A process according to claim 13, where the high-boiling component and hydrogen are contacted at a pressure within a range of about zero psig to 3,000 psig.

19. A process according to claim 13, where the high-boiling component and hydrogen are contacted at a pressure within a range of about 250 psig to 1,000 psig.

20. A process according to claim 13, where the ratio of the weight of the high-boiling component to the weight of the hydrogen gas is within a range of about 0.1:1 to 1000:1.

21. A process according to claim 13, where the ratio of the weight of the high-boiling component to the weight of the hydrogen gas is within a range of about 1:1 to 500:1.

22. A process according to claim 13, where the high-boiling component results from the reaction of methyl chloride with silicon.

23. A process according to claim 13, where the high-boiling component comprises polysilanes and silalkylenes.

24. A process according to claim 13, where the high-boiling component comprises polysilanes described by formula $R_aH_bSi_nCl_{2n+2-a-b}$, where each R is a radical independently selected from a group consisting of alkyls comprising one to six carbon atoms. n=2 to 20, a=0 to 2n+2, b=0 to 2n+2, and a+b=0 to 2n+2.

25. A process according to claim 13, where the high-boiling component comprises silalkylenes comprising one or more silalkylene bonds described by formula $Si(C)_zSi$ and z=1, 2, or 3.

26. A process according to claim 13, where the high-boiling component comprises soluble and insoluble compounds of copper, aluminum, and zinc.

27. A process according to claim 13, where the monosilanes comprise diorganodichlorosilane and organotrichlorosilane and the ratio of the diorganodichlorosilane to the organotrichlorosilane is greater than about 1.0.

28. A process according to claim 9, where R is methyl.

29. A process according to claim 24, where R is methyl.

30. A process according to claim 1, where the organochloride is methyl chloride and the high-boiling component comprises polysilanes, silalkylenes, silicon containing solids, and soluble and insoluble compounds of copper, aluminum, and zinc.

31. A process according to claim 13, where the organochloride is methyl chloride and the high-boiling component comprises polysilanes, silalkylenes, silicon containing solids, and soluble and insoluble compounds of copper, aluminum, and zinc.

* * * * *